United States Patent [19]
Hüttmann

[11] Patent Number: 5,116,124
[45] Date of Patent: May 26, 1992

[54] MEASUREMENT SYSTEM FOR SCATTERING OF LIGHT

[75] Inventor: Horst Hüttmann, Uetersen, Fed. Rep. of Germany

[73] Assignee: Vaisala Oy, Helsinki, Finland

[21] Appl. No.: 663,785

[22] Filed: Mar. 4, 1991

Related U.S. Application Data

[63] Continuation of Ser. No. 404,619, Sep. 8, 1989, abandoned.

[30] Foreign Application Priority Data

Sep. 8, 1988 [FI] Finland .................. 884142

[51] Int. Cl.⁵ .................. G01N 21/00; G01S 13/00
[52] U.S. Cl. .................. 356/342; 356/5; 342/26
[58] Field of Search .......... 356/335, 343, 342, 4.5, 356/375, 5, 152; 350/96.23, 96.27, 316.1, 574, 227.28; 342/26; 250/316.1, 574, 227.28

[56] References Cited

U.S. PATENT DOCUMENTS

| | | | |
|---|---|---|---|
| 3,519,354 | 7/1970 | Brown, Jr. et al. | 356/342 |
| 3,782,824 | 1/1974 | Stoliar et al. | 356/342 |
| 3,788,742 | 1/1974 | Garbuny | 356/342 |
| 3,940,608 | 2/1976 | Kissinger et al. | 250/227.28 |
| 4,099,875 | 7/1978 | McMahon et al. | 250/574 |
| 4,154,529 | 5/1979 | Dyott | 356/342 |
| 4,611,917 | 9/1986 | Robieux et al. | 356/375 |
| 4,711,578 | 12/1987 | Chaimowicz | 356/375 |
| 4,722,599 | 2/1988 | Frungel et al. | 356/342 |
| 4,914,310 | 4/1990 | Tarojski | 356/343 |

Primary Examiner—Richard A. Rosenberger
Assistant Examiner—Hoa Pham

[57] ABSTRACT

This invention concerns an apparatus for the measurement of the parameters of atmospheric visibility or optical density. The apparatus includes a transmitter with which light operating as the measurement signal can be emitted to the measured space; a receiver with which light backscattered from the measured space can be received; and an information processor with which the information of light received by the receiver can be processed and interpreted. According to the invention the active surfaces of the transmitter and receiver means are aligned along an at least essentially same optical axis.

8 Claims, 10 Drawing Sheets

MEASUREMENT SYSTEM FOR SCATTERING OF LIGHT

This application is a continuation of application Ser. No. 07/404,619 filed on Sep. 8, 1989, now abandoned.

BACKGROUND OF THE INVENTION

1. Field of the Invention

The present invention relates to a measurement system for scattering of light.

The system, in accordance with the invention, can be used for measuring the backscattering of light in a vertical, horizontal or freely selectable direction. It can be used for measuring cloud heights, visibility in desired direction, stratifications and contamination layers in the atmosphere as well as for measuring all forms of rain or similar physical parameters that lend themselves to measurement by means of scattered light. The system is applicable in meteorology and environmental protection as well as in the improvement of traffic safety, especially in the air, on roads and seaways, in addition to other sectors having needs for the measurement of similar environmental parameter values.

2. Description of Background Art

Conventional measurement systems for scattered light comprise a separate transmitter and receiver, which are aligned along essentially separate optical axes. The state of prior art technology will be described below in detail with the help the attached drawings.

A basic disadvantage of the prior art technology is that the computation of distance dependence in the received signal requires several assumptions to be made on the character of single and multiple scattering.

In addition to this basic disadvantage, conventional measurement systems bear the following technical problems:

The measurement system comprises two separate optical systems, whereby two sets of tubes, lenses or mirrors, windows (for exit and re-entry of radiation) as well as control mechanisms are required.

The mechanical stability of optical adjustments has an immediate effect on the measurement sensitivity. Hence, a deviation in the parallel alignment of optical axes as a result of a mechanical distortion will immediately be reflected as a change in the overlap function of beams. This further necessitates a sturdy mechanical construction resulting in a voluminous use of construction materials.

Both the transmitter and receiver optics must be adjustable; in addition, the optical axes must be aligned parallel in two planes.

Inhomogeneity of transmitter emission pattern, which is typical in semiconductor lasers, may lead to significant changes in measurement sensitivity especially in the distance range of 300 ... 500 m.

The quality of selected optical components must be matched. For instance, a wedge error in one of the external windows (exit or entry window) may cause a nonparallelism error in the alignment of optical axes.

The distance from the light transmitter, conventionally a semiconductor laser, to the receiver conventionally a photodiode, is determined by the displacement of the optical axes. Together with the massive mechanical constructions required to achieve the desired stability in this kind of an arrangement, substantial electromagnetic disturbance will be conducted from the laser electronics into the circuitry of the receiver photodiode.

SUMMARY OF THE INVENTION

The present invention aims to overcome the disadvantages involved in the afore-described technology and to achieve an entirely novel measurement system for scattered light.

The invention is based on aligning both the transmitter and receiver on a single, or essentially single optical axis. In the preferred construction, the active surfaces of the transmitter/receiver unit are also placed at the focal point of the collimating and focusing optics, or at least close to the focal point. The active surfaces are either parallel-aligned, concentrically annular or a single surface acting as both the transmitting and receiving surface.

When using the concentric optics, light transmission and reception may have different angles of exit/acceptance cones, while the active cross-section at any distance along the optical axes is aligned concentrically along the optical axis. Therefore, the concentric optics is by the nature of physics laws self-aligning.

The measurement apparatus in accordance with the invention comprises a single optic system. Thence, only a single set of tubes, lenses or mirrors, external windows, control mechanisms and other optic components necessary for the implementation of a single unit is required in each measurement apparatus.

The mechanical stability of the optic adjustment has only a secondary effect on the measurement sensitivity, since the possible errors always have an almost equal effect both on the transmitter and receiver channels. The apparatus is in this sense self-compensating.

The quality of selected optical components such as the filter and lens, and especially the external window (placed in the apparatus enclosure) is further less critical than in conventional measurement equipment. The bidirectional passage of light, that is, during exit and entry through the optical system, accomplishes automatic error correction to a degree.

The measurement apparatus necessitates minimal optical adjustment. Control of the transmitter beam cross-section to a desired diameter at a certain distance is all that is needed.

The measurement apparatus features an overlap function with an almost constant value over the entire measurement range. As a result thereof, the sample volume can be assumed constant over the entire measurement range.

Use of a semiconductor laser coupled to an optical fiber ensures a high level of homogeneity in the trnasmitted light emission.

Use of optical fibers in the light-emitting transmitter and light-radiation receiver facilitates the placement of associated electronics components to optimum distances, thus minimizing the risk of electromagnetic disturbance.

The connection of the receiver diode and the semiconductor laser with conventional optical fiber connectors to the optic system permits the replacement of these components without the need for optical re-alignment.

By virtue of the small size achieved by the use of common optics for transmission and reception of light, the measurement apparatus can be used equally in permanent applications on airfields, oil drilling platforms, in automatic weather stations, and similar places, as well as in mobile applications installed in vehicles or similar platforms.

The concentric optics can avail of an integrated transmitter/receiver semiconductor component, in which a single surface both transmits and receives the light.

With the help of optical fibers, the light-receiving fibers can be organized at the receiving surface into concentric rings, whereby the signals from different reflection paths can be received at different divergence angles. This arrangement facilitates the comparative measurement of differences between single and multiple scattering. The advantage of this facility is that the different paths of light rays measure different parts of the atmosphere, whereby the measured differences in the paths give a measure for the divergence of the beam emitted from the apparatus. The difference is dependent on the magnitude of multiple scattering, which further bears correlation with the size of light-dispersing particles.

Furthermore, the use of optical fibers allows combining several light-emitting transmitter heads with a single receiving head into a common head for measurements at different wavelengths with different polarizations or angles of measurement cones.

A single apparatus aligned on a single optical axis can contain a visibility meter and a ceilometer, whereby the meters of different functions can operate using the same or different wavelengths.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 4a shows a conventional apparatus implementing the coincidence function illustrated in FIG. 3;

FIG. 4b shows the case of 90% overlap in the system illustrated in FIG. 4a;

DETAILED DESCRIPTION OF THE PREFERRED EMBODIMENTS

Figure 1:
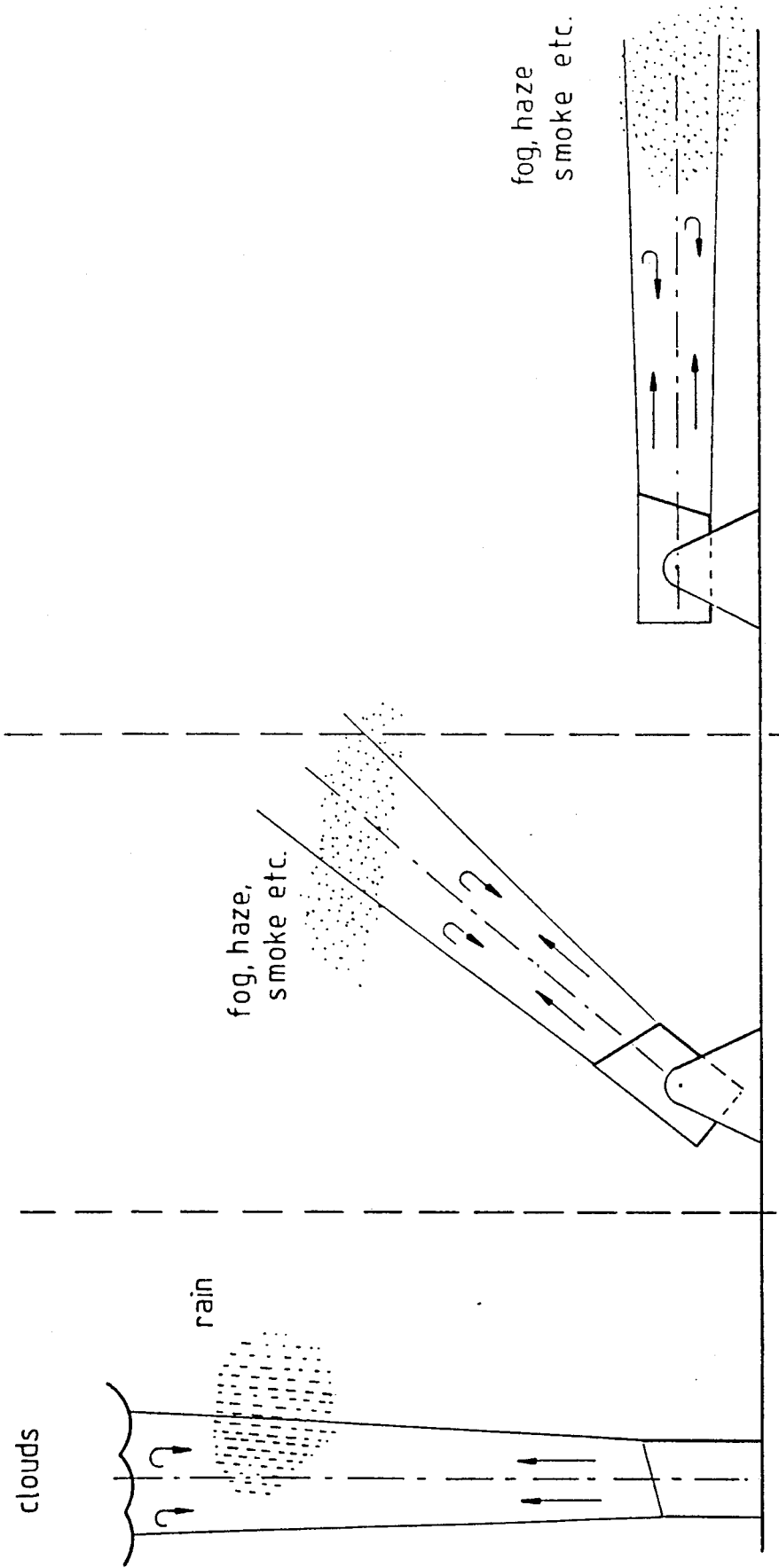
FIGS. 1a, 1b, and 1c show in diagrammatic form the different applications of the system in accordance with the invention.

FIG. 11 shows a second alternative for a branching arrangement of light paths in accordance with a invention; and Illustrated in FIG. 1a is a ceilometric measurement of cloud heights, in FIG. 1b a slant visibility measurement and in FIG. 1c a horizontal visibility measurement.

Figure 2:
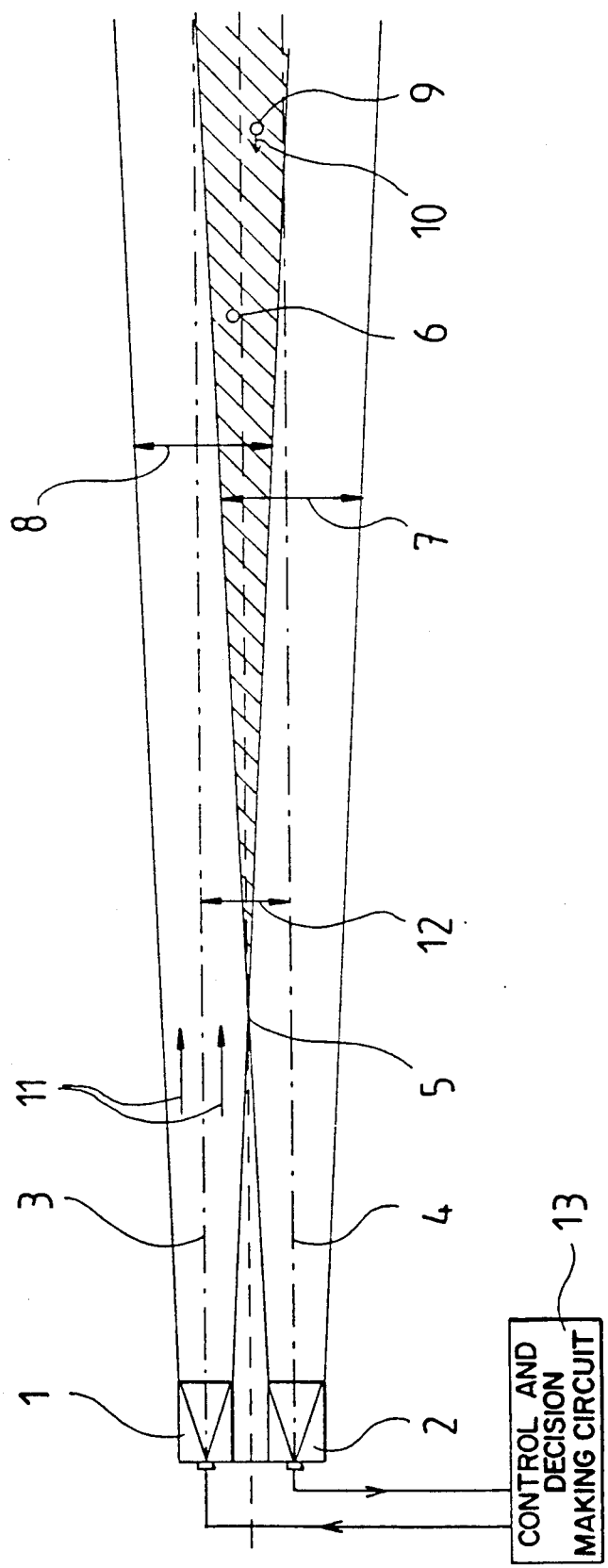
FIG. 2 shows in a side view a measurement system, in accordance with the invention, for scattering of light.

Illustrated in FIG. 2 is a typical construction of a conventional measurement system for scattering of light in the atmosphere. This kind of a system comprises a separate optical system 1 for light transmission. Subsequent reception of a light component 10 backscattered from a particle 9 of the atmosphere takes place with the help of a receiving optic system 2. The systems are generally adjusted so that the optical axis 3 of the transmitter and the optical axis 4 of the receiver are parallel. The distance between the optical axes is designated by reference number 12. Both of the optical systems, that is, the transmitter optics 1 and receiver optics 2, are generally focused to infinity necessitating the closest possible proximity of the exit and acceptance cones, that is, the acceptance cone angle 7 of the receiver and the exit cone angle 8 of the transmitter, within the limitations set by the selected optical components and dimensions of the construction. This kind of an optical system has an overlap function which is distance-dependent as illustrated in FIG. 3.

In the measurement system illustrated in FIG. 2, a short light pulse is emitted from the light transmitter of the transmitter optics 1 toward a direction 11. When a portion of this light pulse meets a particle 9 falling within the transmitter's exit beam cone angle 8, a further portion of this incident light is backscattered in a direction 10. With the assumption that this backscattered portion of the light will not anymore be subjected to further scattering or absorption, the light can be received with the receiver optics 2 as long as it falls into the acceptance cone 7 of the receiver. Explained in other words, this means that single scattering of light can be measured in an overlap space 6. The scattered signal received in the apparatus will be processed in the control and decision-making unit 13. The overlap space will extend from a point 5 which is the same as the point A on the distance axis in FIG. 3. Any scattered light from the space remaining closer to the receiver than this point can be detected only for that portion which is scattered from a plurality of particles, that means, from at least two particles.

Figure 3:
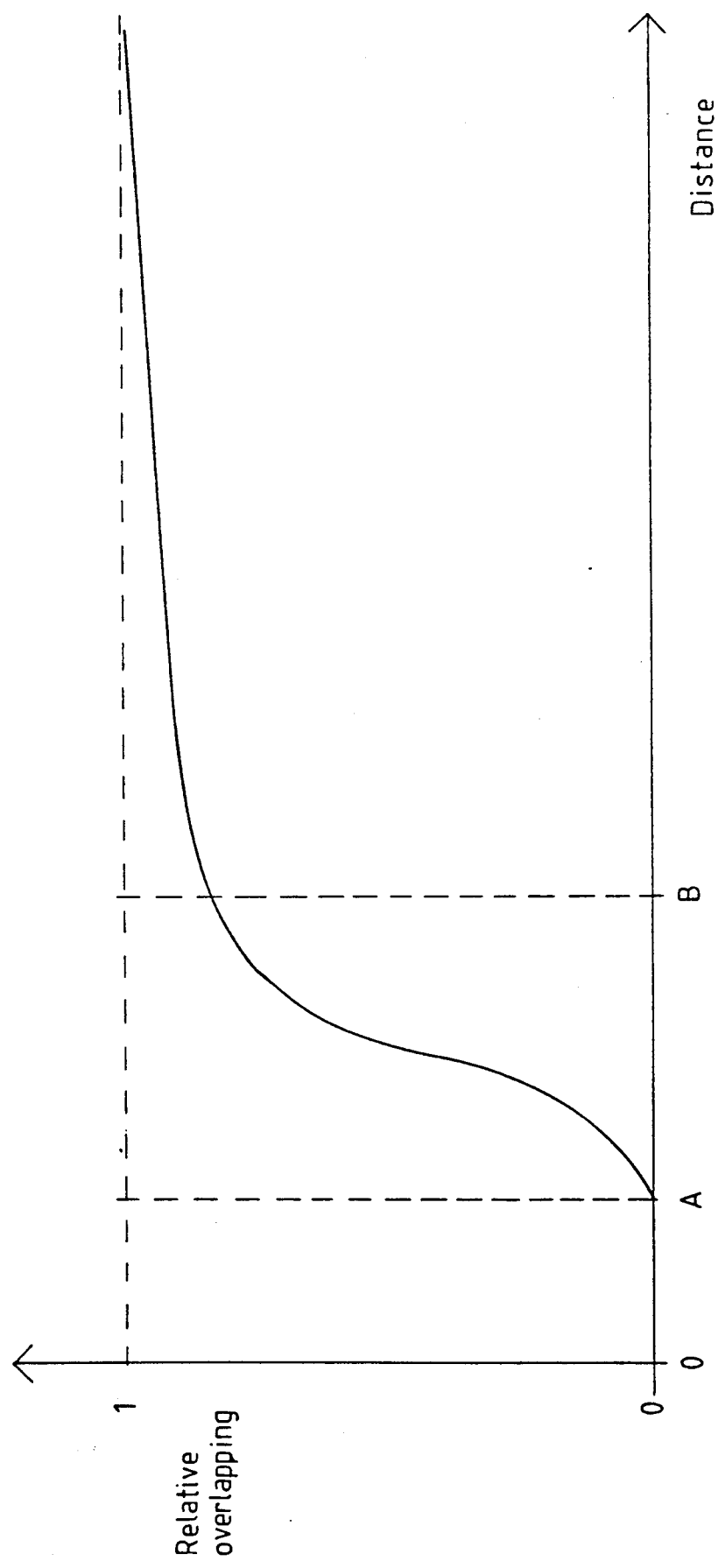
FIG. 3 shows in a graph the overlap function of a conventional measurement system for scattering of light.

A significant disadvantage of the above-described conventional technology is the sharp rise of the overlap function between points A and B as illustrated in FIG. 3. This rise characterizes the increase in the measured volume and indicates that a small change in measurement distance within the area illustrated in FIG. 3 from point A to point B will cause a substantial change in the received signal. The receiver is to be conceived as the receiver optics 2 illustrated in FIG. 2. illustrated in FIG. 3 is the range A–B which in practice has a distance value of 20–50 m for point A, while point B is situated at a distance of 300–500 m. Therefore, measurement equipment implemented using conventional systems present their maximum error within a range extending up to a measurement distance of 300–500 m, which also is their most important operating range as dictated by the conditions of aviation and other traffic.

Figures 4A, 4B:
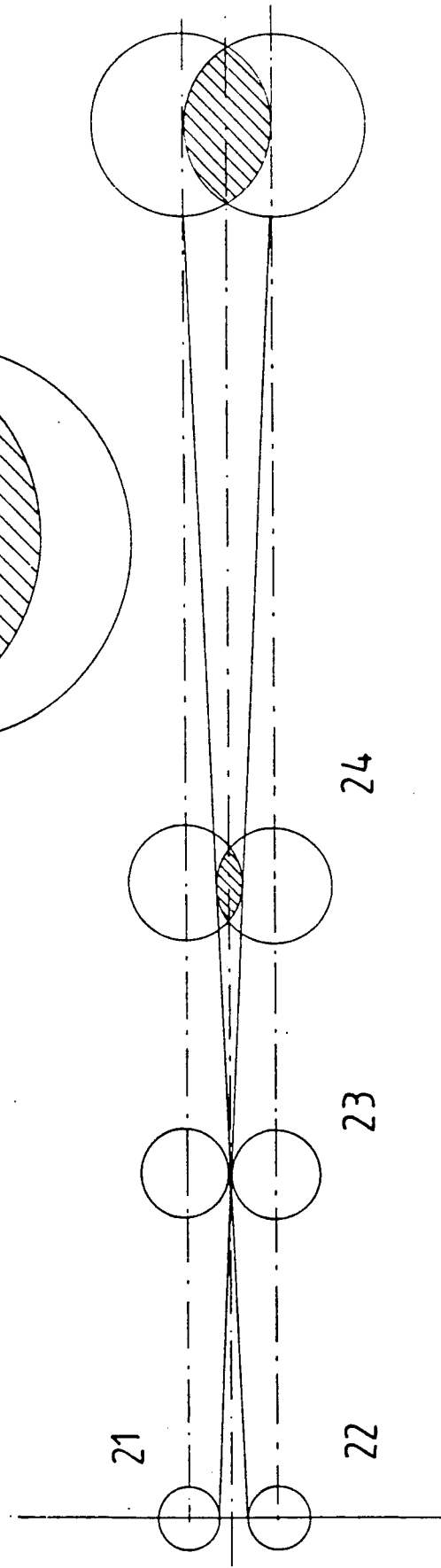

Illustrated in FIGS. 4a and 4b is the construction of a transmitter and receiver which implements the overlap function shown in FIG. 3. The transmission/reception reference plane 20 is situated to the left in the figure. The optical axis 21 of the transmitter is placed above the optical axis 22 of the receiver. Overlapping starts at point 23 and progresses into a partial overlapping at point 24, which also represents a point within the range A-B depicted in the graph of FIG. 3. The 90% overlap situation is shown in FIG. 4b.

Figure 5:
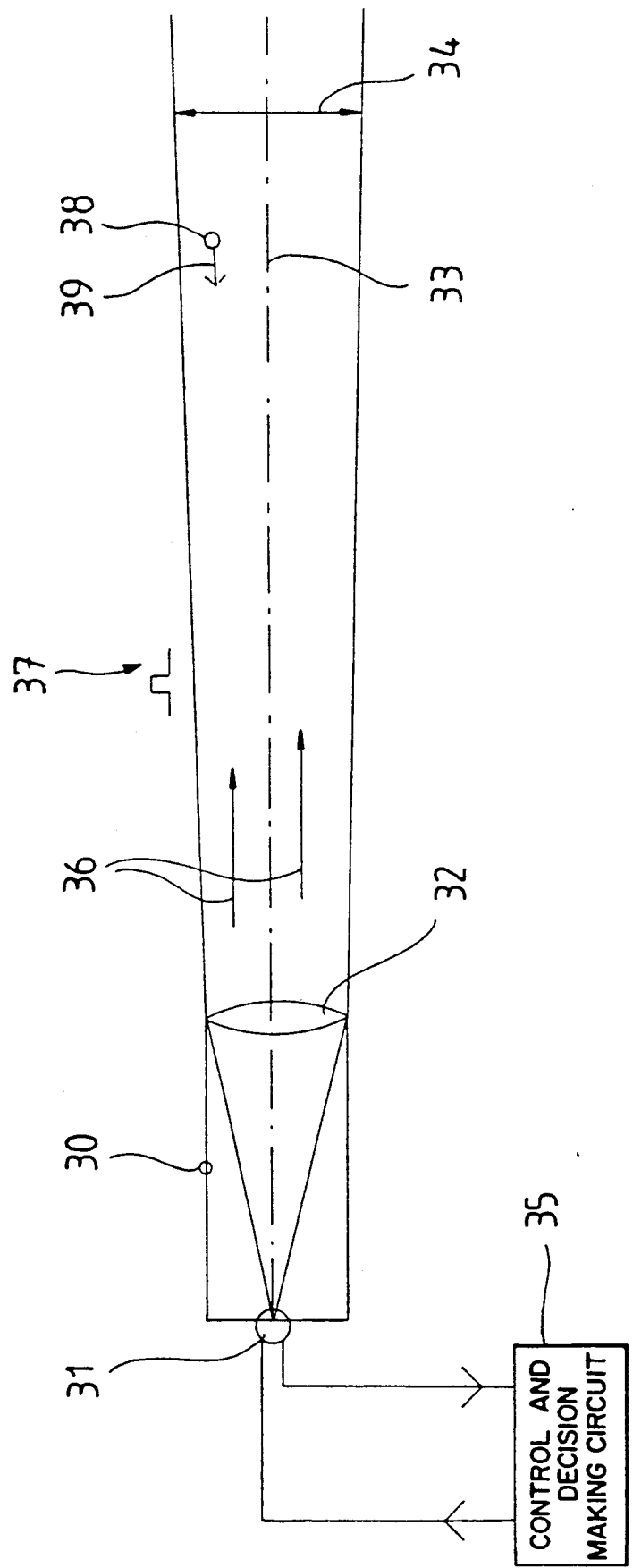
FIG. 5 shows in a diagrammatic side view the main components of an apparatus in accordance with the invention.

As illustrated in FIG. 5, the main component in the measurement apparatus in accordance with the invention is a transmission/reception arrangement 30 of light in which a combination transmitter/receiver 31 is placed at or at least close to the focal point of a focusing optic system 32, whereby both the light transmitter and receiver have a common optical axis 33, together with a minimum angle 34 of the exit/acceptance cone. The focusing optics 32 can in this embodiment be a double-convex lens. The transmitter/receiver 31 is controlled by a control and decision-making electronics unit 35. The propagation direction of emitted light pulse is indicated by arrows 36, while reference number 37 refers to a diagrammatic waveform of the transmitted pulse. A backscattering particle 38 falling within the measurement area scatters light toward a direction 39.

The operation of the measurement apparatus is based on propagation time measurement. As illustrated in FIG. 5, a short-duration light pulse 37 emitted toward the direction 36 from the light transmitter/receiver unit 30 penetrates atmosphere falling within an angle 34 of the transmisson beam cone. A part 39 of the light incident on the particle 38 will be backscattered. This part can be received by the reveiver unit 30. The electronic time measurement from the transmission instant of the light pulse to the instant at which light hits the particle then gives information on the distance of scattering particles from the measurement apparatus. The amplitude of the backscattered light pulse provides a measure for the cross-section of the active backscattering area which in real conditions is also influenced to some extent by the size and quantity of particles. The measurement sequence performed by the measurement apparatus is controlled by the control and decision-making electronics unit 35.

Figure 6:
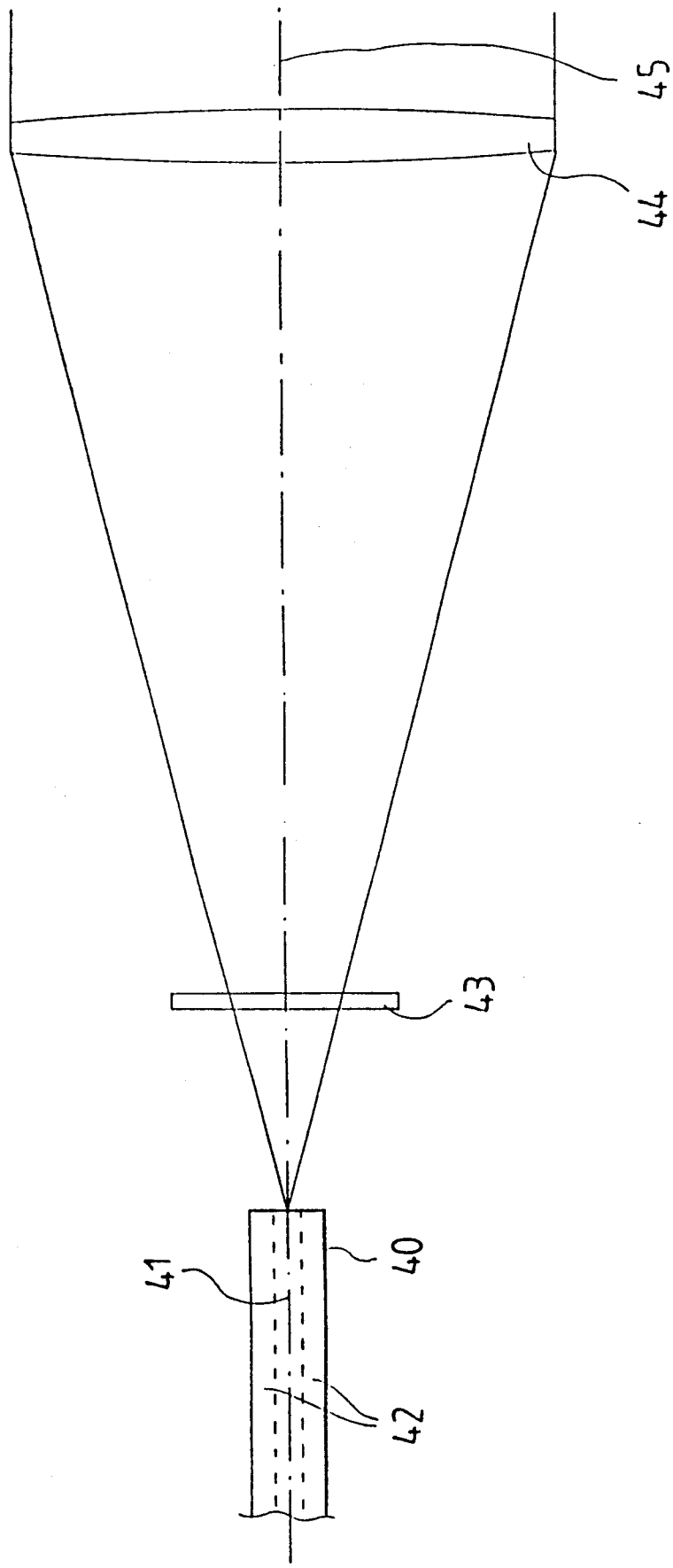
FIG. 6 shows in a diagrammatic side view the optical components of the apparatus in accordance with the invention.

Illustrated in detail in FIG. 6 is the optical construction of the measurement apparatus. The optical axis is designated by reference number 45. A lens 44 forms simultaneously the exit aperture for the light radiation emitted toward the measured area and the entry aperture for the backscattered part of the light pulse. The focal length of the lens is selected sufficiently long so that the angle of incidence on a filter 43 is practically orthogonal, whereby transmission distortions in the filter are avoided. The actual active area of transmission/reception in the measurement apparatus is provided by the combination end of an optical fiber bundle 40. The structure of the fiber bundle comprising a transmitter fiber 42 surrounded by several receiver fibers is illustrated in detail in FIG. 7.

Figure 7:
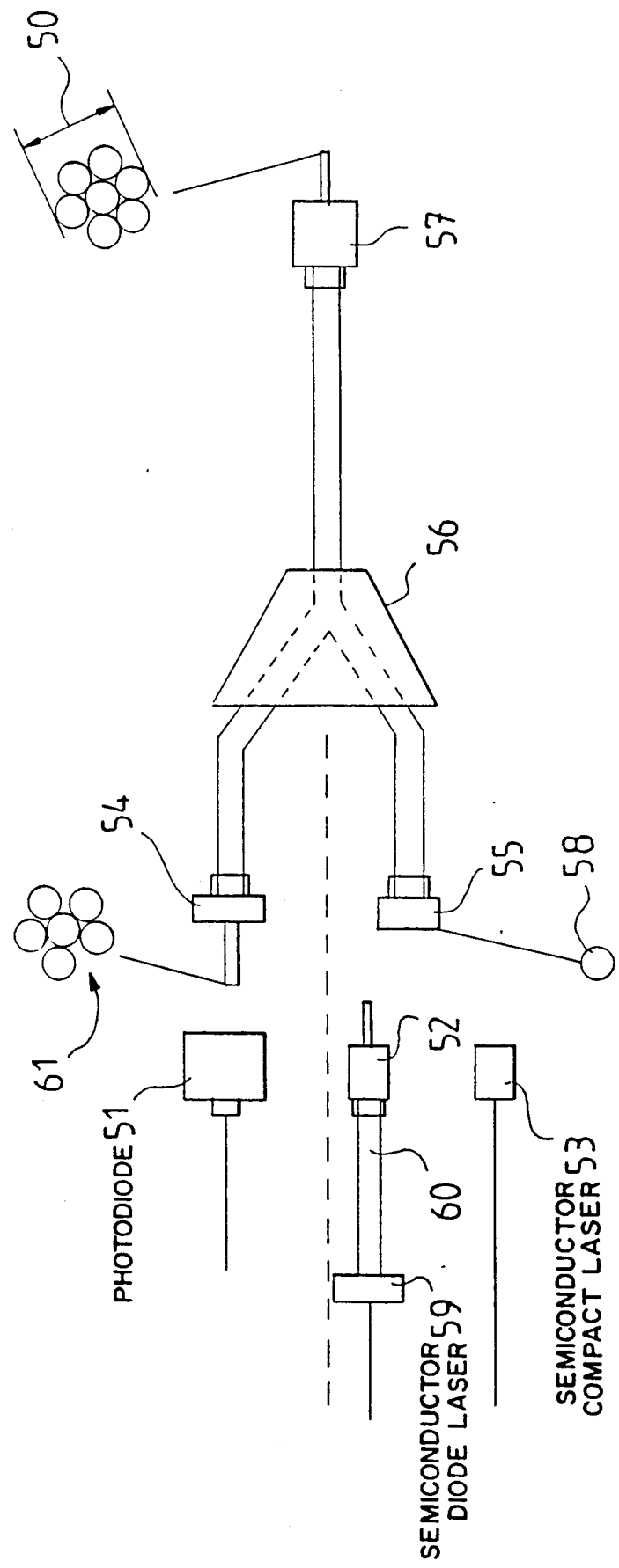
FIG. 7 shows in detail the components of optical connections in the apparatus in accordance with the invention.

As illustrated in FIG. 7, the fiber bundle is fabricated from fibers having a core diameter greater than 200 $\mu$m using the methods of conventional technology. At this stage care must be taken to keep the total diameter 50 of the fiber bundle compatible with the diameter of the focal point area of the lens 44 shown in FIG. 6.

The selection of optical components described above, together with their arrangement in the optical system, results in an almost identical cone angle for both the transmitter and receiver as illustrated by the cone angle 34 in FIG. 5. A consequence thereof is that the overlap function can be assumed constant over the entire measurement range.

Illustrated in FIg. 7 is a plug-in connector 57 for easy attachment of the optical fiber bundle to the optical system tube. A member 56 is provided for supporting the branching area of the fiber bundle, the branching of the transmission fiberes from the six receiver fibers of the the illustrated embodiment. The only transmitter fiber 58 is terminated in a plug-in connector 55, thus facilitating an easy replacement of the light source. The light source can be a semiconductor diode laser 59, connected via an optical tail fiber 60 and a plug-in connector 52, or alternatively, a compact semiconductor laser 53 having an integral lens in the plug-in connector (type SELFOC, Reg. TM).

Receiver fibers branching from the support member 56 of the branching point of the fiber bindle are terminated in the plug-in connector 54. At this end of the bundle the receiver fibers are arranged so as to obtain a minimum diameter of the bundle. A photodiode 51 is connected to the plug-in connector 54. A cross-section 61 in the figure illustrates the arrangement of the receiver fibers.

Figure 8:
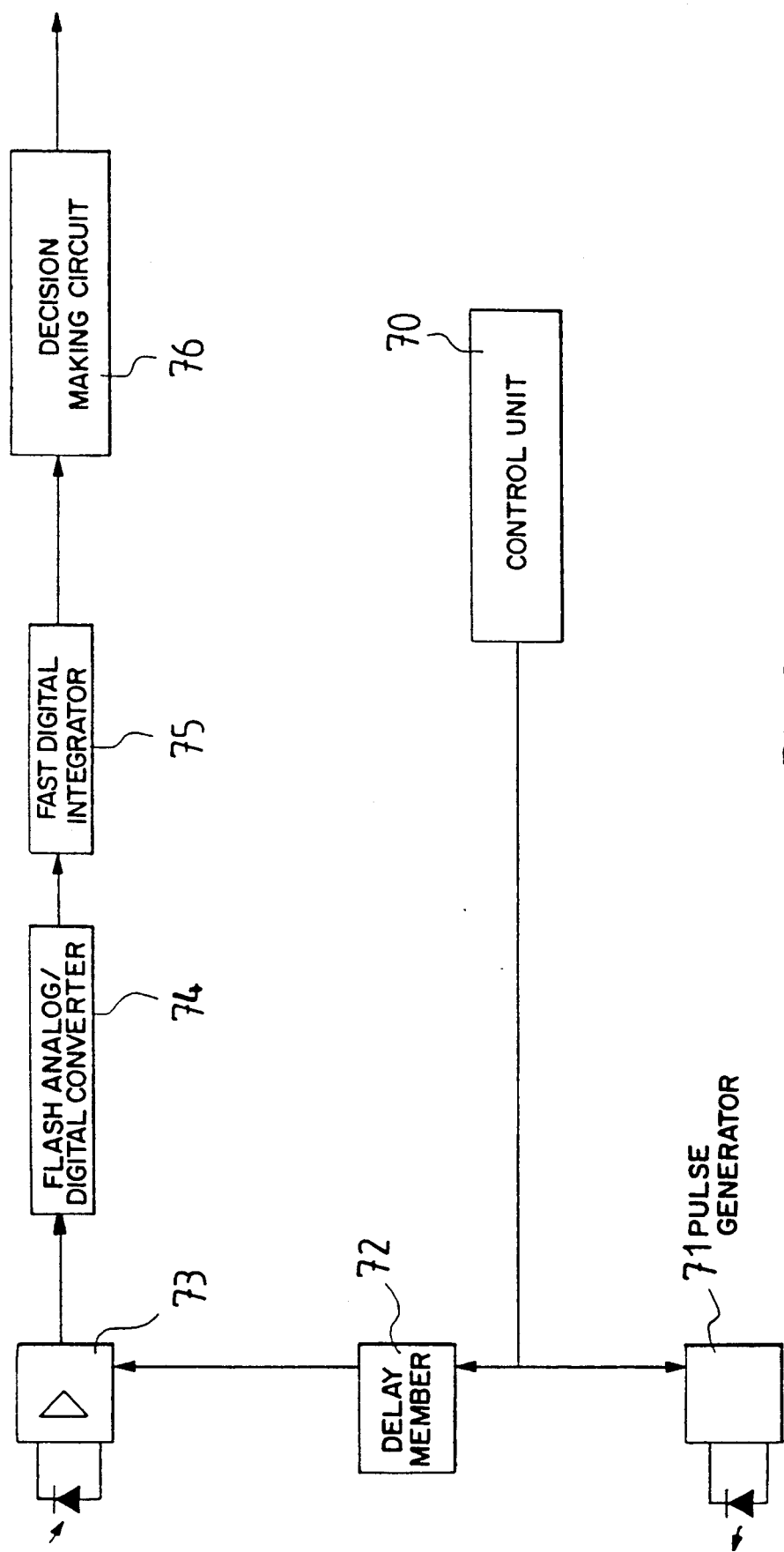
FIG. 8 shows the principal blocks of control and decision electronics in the apparatus in accordance with the invention.
Figure 9:
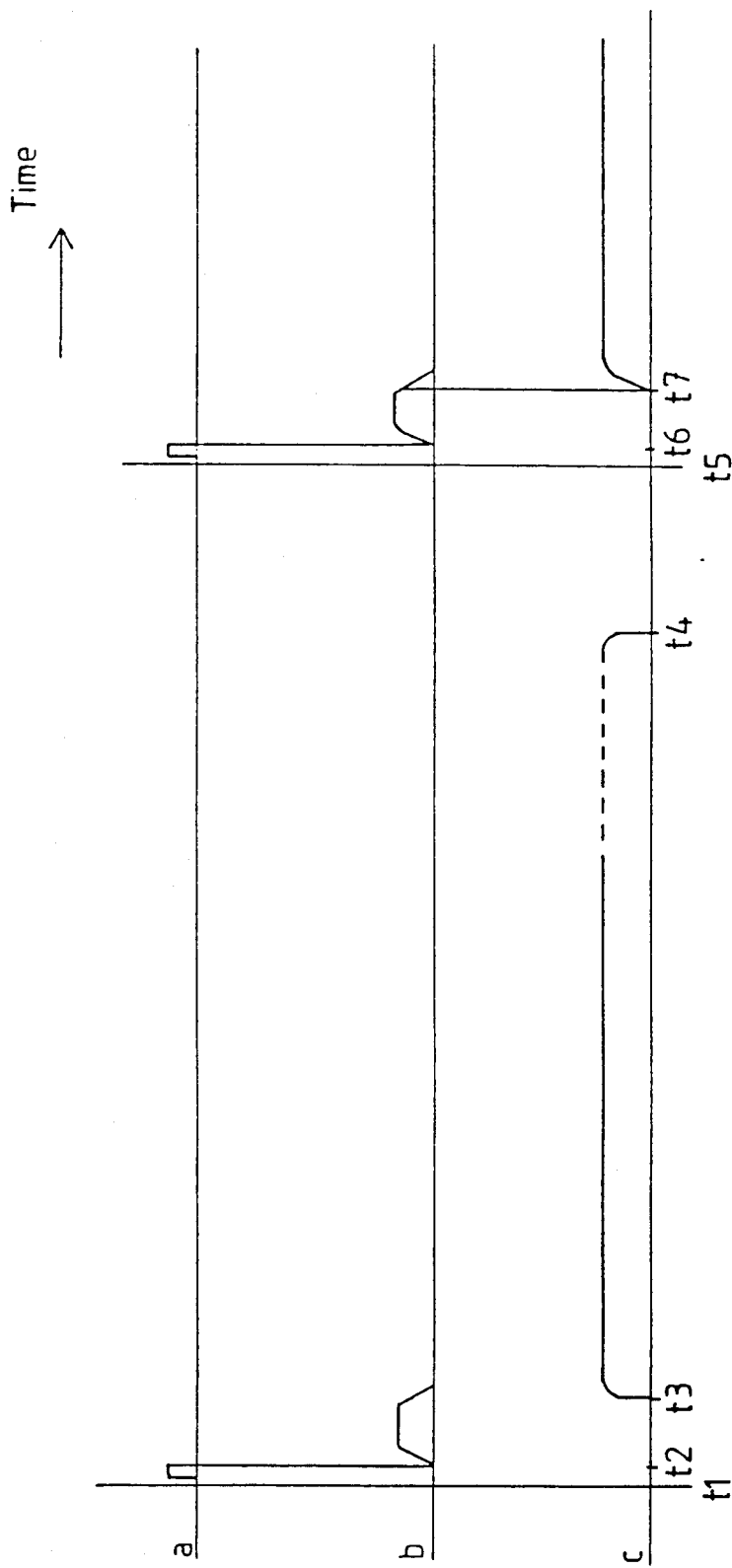
FIG. 9 shows the timing diagram for the electronics illustrated in FIG. 8.

Illustrated in FIg. 8 is the basic configuration of the control and decision-making electronic circuitry, while FIG. 9 illustrates the timing sequence of the measurement. A control unit 70 serves to control the timing of the measurement sequence. At instant $t_1$ the control unit outputs a trigger pulse. This trigger pulse is taken to a pulse generator 71 of the laser and to a delay member 72. At the falling edge of the trigger pulse, designated by $t_2$, a laser pulse is issued from the pulse generator 71 to the laser connected to the transmitter fiber. The purpose of the delay member 72 is to provide sufficient delay up to instant $t_3$ which desingates the falling edge of the laser pulse. Another trigger pulse is further issued from the delay member to the receiver amplifier 73 determining the sampling of the light amplifier by electronic means. The light amplifier will sample up to instant $t_4$. The instant $t_4$ is selected so as to allow the light pulse from the laser to travel the distance selected in the measurement apparatus twice, that is, once forward and once backscattered. Backscattered portions of light received between instants $t_3$ and $t_4$ are detected and amplified in the receiver amplifier 73 and routed to a flash analog-digital converter 74. The analog-digital converter 74 outputs digital measurement values to a fast digital integrator 75. During the time interval $t_3 - t_4$ the system can perform, e.g., 255 analog-to-digital conversions allowing the entire measurement range to be divided into 255 increments of measured distance.

· The above-described measurement sequence will be restarted at instant $t_0$. This sequence is then identical to that described above.

The measurement process will be concluded when the digital integrator 75 has by integration (within the resolution of selected number of increments of measured range) compiled from the single measurement samples a digital pattern of the backscattering profile with a sufficient discrimination from noise. This backscattering profile is then routed to a decision-making unit 76. The decision-making unit finally computes values for the desired measurement parameters by mathematical means.

Within the scope of the invention, the optical construction of the measurement system illustrated in FIG. 6 can be modified for the use of mirror optics.

In the embodiment of the invention, the fiber bundle structure illustrated in FIG. 7 is not decisive. An alternative possibility is to fuse the fiber ends so as to obtain a single fiber with a larger diameter.

Figure 10:
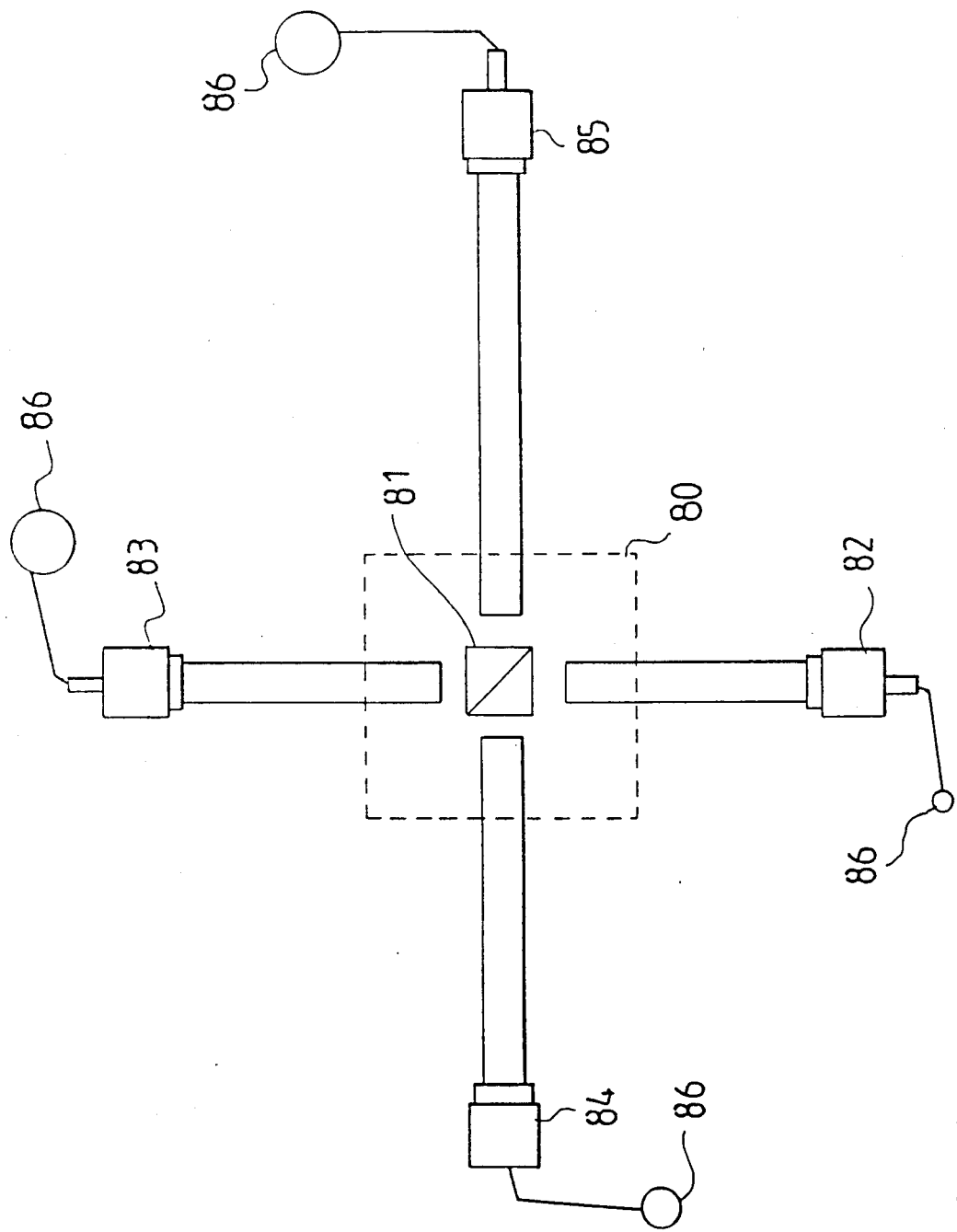
FIG. 10 shows a first alternative for the branching arrangement of light paths in accordance with the invention.

As illustrated in FIG. 10, the branching of radiation paths at the transmitting and receiving ends can also be attained with the help of standard optical components such as beam splitters. This construction offers multiple possibilities for the use of, e.g., polarizing filters or optical switches in order to minimize internal reflections in the apparatus. In the designations used in FIG. 10, reference number 80 refers to the enclosure of the beam splitter, number 81 to the beam splitter, number 82 to the end of the monitoring fiber of laser operation, number 83 to the end of the receiver fiber with its plug-in connectors, number 84 to the end of the transmitter fiber with its plug-in connectors, number 86 to the cross-section of the fiber, and number 85 to the combination end of transmitter and receiver fibers with the plug-in connector.

The use of an optical fiber bundle offers the possibility of organizing the fibers of the combination end, namely, the transmitter/receiver end, into concentric rings, from which each ring is branched into a separate receiver branch as illustrated in FIG. 11. At least in the near measurement range, this arrangement offers the measurement of signal differences for the purpose of discrimination between single and multiple scattering. Reference number 90 in FIG. 11 designates the end of the fiber bundle of the first receiver channel with the plug-in connector. This bundle contains the twelve fibers of the outer ring. Designated by reference number 91 is the cross-section of the transmitter fiber, while reference number 92 designates the cross-section of the combination transmitter/receiver bundle. The receiver fibers are arranged into two concentric rings having six and twelve fibers, respectively. Reference number 93 designates the end of the fiber bundle of the second receiver channel with the plug-in connector. This bundle contains the six fibers of the middle ring. Reference number 94 designates the end of the transmitter fiber with the plug-in connector, number 95 designates the support member of the fiber branching, and number 96 designates the end of the combination transmitter/receiver fiber bundle with the plug-in connector.

The use of fiber bundles in coaxial optic systems offers the possibility of constructing a measurement apparatus which ultilized light sources emitting at several different wavelengths. Furthermore, the benefits of different polarization planes can be exploited. Moreover, different control methods using, e.g., pulses or modulated light sources are possible. In addition, it is possible to use different kinds of reception techniques in conjunction with a single transmission technique in the same measurement apparatus, thus allowing the techniques for far-range measurements (with the purpose of indicating a possible backscattering without the need for exact measurement of signal amplitude), while near-range measurements are simultaneously performed applying the exact methods of quantitative measurements.

The optic system in accordance with the invention is equally applicable for use with pulsed as well as intensity and transit time measurements (LIDAR) or in conjunction with a continuously emitting light source.

A portion of the internally reflected part of light emitted from the light source can be used for monitoring the functions of the apparatus in order to, e.g., stabilze the light output or adjust receiver sensitivity.

The coaxial optic system in accordance with the invention is constructable using optical fibers in bundles, fused, parallel aligned, concentrically arranged into rings or other formations so that the fibers can be assembled into a single combination head, which operates as the active transmitting and receiving surface. Furthermore, the fibers are routed into at least two, possibly a greater number of separately branching fiber bundles for light launching and reception. The optical fibers used are of the "step-index" type (having a stepwise incrementing refractive index toward the outer circumference) or of the "graded-index" type (having a refractive index increasing gradedly toward the outer circumference) of multimode optical fibers having a large outer diameter. The material of the fibers is preferredly of glass or other suitable material which is compatible with the requirements of optical power transmission and large variations in temperature and humidity.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for the measurement of parameters of atmospheric visibility or optical density within a measured space of atmosphere comprising:

pulse transmitter means for transmitting pulsed light into the measured space;

receiver means for receiving backscattered light from the measured space;

focusing optics, serving as both transmit and receive optics, for directing said pulsed light toward a desired object within the measured space and for directing said backscattered light onto an active surface of said receiver means; and information processing means for processing and interpreting intensity and delay information of said backscattered light to generate the parameters and for controlling the apparatus, comprising control means for generating a trigger pulse, pulse generating means, coupled to said control means, for directing said pulse transmitter means to transmit said pulsed light after receipt of said trigger pulse, and delay means, coupled to said control means, for delaying said trigger pulse to enable said receiver means for a period, the onset of which coincides with a falling edge of said pulsed light, active surfaces of said transmitter means and said receiver means abut one another and are aligned in concentric circles along essentially the same optical axis allowing a single optics system to function as said focusing optics.

2. The apparatus for the measurement of parameters of atmospheric visibility or optical density of claim 1, said active surfaces positioned at the focal point of said single optics system 3. The apparatus for the measurement of parameters of atmospheric visibility or optical density of claim 1, said information processing means further comprising:
 a flash analog/digital converter, coupled to said receiver means, for converting said received backscattered light into digital measurement values;
 fast digital integration means, coupled to said flash analog/digital converter, for integrating said converted baskscattered light into information indicative of a digital backscattering profile; and
 decision means, coupled to said fast digital integration means, for generating the parameters based upon said digital backscattering profile.

4. An atmospheric optical measurement system for measuring atmospheric particle density comprising:
 pulse transmitter means for transmitting pulsed measurement light into a predetermined area of atmosphere;
 receiver means for receiving said pulsed measurement light as backscattered light reflected from atmospheric particles;
 optical an focusing lens, aligned with said transmitter means and said receiver means, for focuisng said pulsed measurement light and said backscattered light;
 information processing means, coupled to said transmitter means and said receiver means, for controlling the system and generating parameters indicative of atmospheric particle dnesity comprising
 control means for generating a trigger pulse,
 pulse generating means, coupled to said control means, for directing said pulse transmitter means to transmit said pulsed measurement light after receipt of said trigger pulse, and
 delay means, coupled to said control means, for delaying said trigger pulse to enable said receiver means for a period, the onset of which coincides with a falling edge of said pulsed measurement light; and
 a single self-contained optical fiber bundle consisting of a central transmit fiber and concentric rings of receive fibers abutting one another and said central transmit fiber, for directing said pulsed measurement light from said pulse transmitter means to said optical focusing lens via said central transmit fiber and for directing said backscattered light from said optical focusing lens to said receiver means via said concentric rings of receive fibers.

5. The atmospheric optical measurement system of claim 4, said concentric rings of receive fibers comprising a first concentric ring and a second concentric ring.

6. The atmospheric optical measurement system of claim 5, said receiver means comprising a first receiver and a second receiver, said first receiver operatively coupled to said first concentric ring of receive fibers to provide a first receiver channel and said second receiver operatively coupled to said second concentric ring of receive fibers to provide a second receiver channel.

7. The atmospheric optical measurement system of claim 4, an active surface of said single self-contained optical fiber bundle aligned to be positioned at the focal point of said optical focusing lens.

8. The atmospheric optical measurement system of claim 4, said information processing means further comprising:
 a flash analog/digital converter, coupled to said receiver means, for converting said received backscattered light into digital measurement values;
 fast digital integration means, coupled to said flash analog/digital converter, for integrating said converted backscattered light into information indicative of a digital backscattering profile; and
 decision means, coupled to said fast digital integration means, for generating the parameters based upon said digital backscattering profile.

* * * * *